United States Patent [19]
Knuebel et al.

[11] Patent Number: 5,811,560
[45] Date of Patent: Sep. 22, 1998

[54] PROCESS FOR THE PRODUCTION OF 8α, 12-OXIDO-13, 14,15,16-TETRANORLABDANE

[75] Inventors: Georg Knuebel; Andreas Bomhard; Thomas Markert, all of Duesseldorf, Germany

[73] Assignee: Henkel Kommanditgesellschaft auf Aktien, Duesseldorf, Germany

[21] Appl. No.: 836,162

[22] PCT Filed: Oct. 27, 1995

[86] PCT No.: PCT/EP95/04225

§ 371 Date: May 5, 1997

§ 102(e) Date: May 5, 1997

[87] PCT Pub. No.: WO96/14310

PCT Pub. Date: May 17, 1996

[30] Foreign Application Priority Data

Nov. 5, 1994 [DE] Germany .......................... 44 39 574.4

[51] Int. Cl.⁶ .................................................. C07D 307/92
[52] U.S. Cl. ............................................................ 549/458
[58] Field of Search ............................................. 549/458

[56] References Cited

U.S. PATENT DOCUMENTS

| | | | |
|---|---|---|---|
| 3,029,255 | 4/1962 | Stoll ..................................... | 260/345.2 |
| 3,050,532 | 8/1962 | Schumacher et al. ............... | 260/343.3 |
| 4,701,543 | 10/1987 | Naef ...................................... | 549/458 |
| 5,274,134 | 12/1993 | Bruns et al. ............................ | 549/458 |

FOREIGN PATENT DOCUMENTS

| | | |
|---|---|---|
| 0 170 955 | 2/1986 | European Pat. Off. . |
| 0 212 254 | 3/1987 | European Pat. Off. . |
| 0 550 889 | 7/1993 | European Pat. Off. . |
| 61-33184 | 2/1986 | Japan . |
| 701 911 | 1/1954 | United Kingdom . |
| WO 90/12793 | 11/1990 | WIPO . |

OTHER PUBLICATIONS

Verstegen–Haaksma et al., Total Synthesis of (–)–Ambrox etc., Tetrahedron, vol. 50 (33), pp. 10095–10106, Aug. 15, 1994.
Tetrahedron 49(28):6251–62(1993).
J. Org. Chem.57:955–60(1992).
Chemistry and Industry 516–520(Aug. 1990).
Ullmanns Encyklopädie der technischen Chemie 20:283(Vertag Chemie, 1981).
Helv. Chim. Acta. 33:1310–12(1950).
Chem. Abstr. 57:7316a(1962).
Chem. Abstr. 94:15913q(1981).
Synthesis 216–19(1983).

*Primary Examiner*—Bernard Dentz
*Attorney, Agent, or Firm*—Wayne C. Jaeschke; Glenn E. J. Murphy; Martin G. Meder

[57] ABSTRACT

The invention pertains to a method for preparing 8-alpha, 12-oxido-13,14,15,16, -tetranorlabdane by cyclizing a mixture of hydroxy-olefins (I)-(III). See the specification for their formulae. The cyclization is carried out in the presence of 10 to 100 wt. % acid, relative to the mixture of compounds (I) to (III).

7 Claims, No Drawings

PROCESS FOR THE PRODUCTION OF 8α, 12-OXIDO-13, 14,15,16-TETRANORLABDANE

BACKGROUND OF THE INVENTION

1. Field of the Invention

This invention relates to a process for the production of 8α,12-oxido -13,14,15,16-tetranorlabdane.

2. Discussion of the Related Art

8α,12-Oxido-13,14,15,16-tetranorlabdane, hereinafter referred as Ambroxan, is a valuable ambergris perfume which is found in ambergris, a metabolic secretion of the sperm whale (Ullmanns Encyklopädie der technischen Chemie, Vol.20, page 283, Verlag Chemie Weinheim 1981). Ambroxan can be synthesized from sclareol by oxidative side chain degradation and subsequent reduction of the lactone formed (sclareolid) in accordance with U.S. Pat. No. 3,050,532. The conversion of sclareolid into the odorless 8α,12-dihydroxy-13,14,15,16-tetranorlabdane, hereinafter referred to in short as diol, is carried out by methods known per se, for example by reduction with lithium aluminium hydride (Helv. Chim. Acta 1950, 33, 1310), with sodium borohydride (Chem. Abstr. 57, 7316a) or with potassium borohydride/lithium chloride mixtures (Chem. Abstr. 94,15913q).

The cyclizing dehydration of the diol to Ambroxan can be carried out with acidic catalysts, for example p-toluene sulfonic acid, p-toluene sulfonic acid chloride, catalytic quantities of sulfuric acid and acidic ion exchangers, in various solvents, for example toluene, hexane, pyridine, tetrahydrofuran or methanol, preferably at boiling temperature.

U.S. Pat. No. 3,029,255 describes the use of β-naphthalene sulfonic acid or alumina as dehydration catalysts in the production of Ambroxan. Besides resinification products and olefins, other secondary production are obtained in this process, so that the yield of Ambroxan is less than 77%.

JP-A-86/33184 (Takasago) describes a process for the production of Ambroxan, in which cyclization of the diol precursor is induced by special catalysts. These catalysts are acid-impregnated active white clay, alumina or silica. The acids mentioned include, above all, sulfuric acid, phosphoric acid and polyphosphoric acid. However, the Takasago process has disadvantages in regard to a) the conversion of educt, i.e. the diol used, and/or b) the formation of dehydration products (secondary products) and/or c) the stereoselectivity of the ring-closing reaction (level of iso-Ambroxan formation).

The above-mentioned disadvantages of the Takasago process are avoided by the process disclosed in applicants' earlier patent application WO 90112793. Nevertheless, the process according to WO 90/12793 requires relatively high reaction temperatures. In addition, the formation of dehydration products cannot be completely avoided.

All in all, it has to be said that dehydration products occur to a more or less large extent in the processes known from the prior art for the production of Ambroxan by cyclization of the diol precursor. According to investigations carried out by applicants, these dehydration products are compounds which can be represented by formulae (I), (II) and (III):

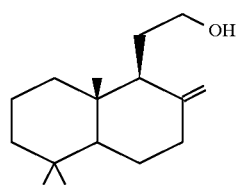

(I)

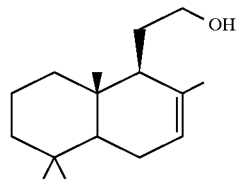

(II)

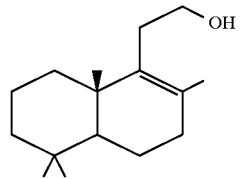

(III)

The dehydration products mentioned are odorless and reduce the yield of Ambroxan obtained in the acidic cyclization of the diol precursor.

It is known from EP-A-212 254 that the compound corresponding to formula (I) can be cyclized in the presence of acidic catalysts to form Ambroxan. Nevertheless, there is nothing in the description of the patent application to show how the cyclization is carried out. In particular, the description does not mention which critical parameters have to be observed to ensure that the cyclization of (I) takes place efficiently.

A.F. Barrero et al. investigated the cyclization of two derivatives of (I) in the presence of acidic catalysts (cf. Tetrahedron, 1993, Vol. 49, No. 28, pages 6251–6262). These derivatives differ structurally from compound (I) in the fact that one of the geminal methyl groups present in (I) is replaced by a group—COOMe or —CH$_2$OH. The cyclization takes place satisfactorily at 0° C. in the highly polar solvent nitromethane. At higher temperatures, however, 8-epi-Ambroxan is preferentially formed.

As far as applicants are aware, the cyclization of compounds (II) and (III) is not described in the literature. Nor is it logical to the expert from a knowledge of EP-A-212 254 and the above-mentioned article by A.F. Barrero et al. The reason for this is that it is known to the expert that reactions which can be successfully applied to a certain compound cannot be automatically applied with the same success to isomeric or analogous compounds. This is also known in particular for the production of stereoisomers of Ambroxan. For example, P.F. Viad and N.D. Ungur investigated the production of 8-epi- and 9-epi-Ambroxan and the production of Ambroxan by ring closure of the corresponding 1,4-diol precursors with dimethyl sulfoxide/chlorotrimethyl silane (cf. Synthesis 1983, pages 216–219). They found that the cyclization yield is largely dependent upon the stereochemistry of the educt. Whereas Ambroxan and its 9-epi-isomer were obtained in yields of 85% and 90%, the 8-epi-isomer was obtained in a yield of only 46%.

DESCRIPTION OF THE INVENTION

The problem addressed by the present invention was to provide a process for cyclizing a mixture of compounds (I), (II) and (III) which would enable Ambroxan to be efficiently obtained by acidic cyclization. Another problem addressed by the present invention was to ensure that the Ambroxan formed in the ring-closing reaction would only contain small quantities of the epimers (8-epi- and 9-epi-Ambroxan) which are of no value as perfumes. The expression "small quantities" in the context of the invention is understood to mean that the epimers of Ambroxan—based on the total quantity of Ambroxan, 8-epi- and 9-epi-Ambroxan—are present in the reaction mixture after cyclization in a quantity of at most 30% by weight.

According to the invention, the problems stated above have been solved by a process for the production of 8α,12-oxido-13,14,15,16-tetranorlabdane by cyclization of a mixture of compounds I, II and III, in which compounds I to III had the structural formulae illustrated in the foregoing. According to the invention, the cyclization is carried out in the presence of 10 to 100% by weight—based on the mixture of compounds I to III used—of an acid.

Accordingly, the present invention relates to a process for the production of 8α,12-oxido-13,14,15,16-tetranorlabdane by cyclization of a mixture of compounds I to III in the presence of 10 to 100% by weight—based on the mixture of compounds I to III used—of an acid. The mixture of compounds I to III should contain at least 10% by weight of each of components I to III, based on the mixture of compounds I to III.

The reaction temperature at which the acidic cyclization is carried out is not critical in the process according to the invention. However, the reaction is preferably carried out at temperatures of −10° to 30° C. This takes account of the fact that, on the one hand, a reaction rate sufficient for practical purposes is guaranteed and, on the other hand, there is no unwanted epimerization of the target substance. In a particularly preferred embodiment, the reaction is carried out at temperatures of 0° to 20° C.

The cyclization catalyst is used in a quantity of—based on the diol—10 to 100% by weight in the process according to the invention. The preferred quantity is in the range from 30 to 60% by weight.

An acid is used as the cyclization catalyst in the process according to the invention. The nature of the acid is not subject to any particular limitations. Thus, any Brönstedt and Lewis acids may be used. However, hydrohalic acids, particularly HCl, and sulfuric acid, p-toluene sulfonic acid and alkane sulfonic acids are particularly preferred. Methane sulfonic acid is most particularly preferred.

Suitable solvents for the process according to the invention are, for example, toluene and/or xylene and halogenated hydrocarbons. Dichloromethane is a particularly preferred solvent.

The following Examples are intended to illustrate the invention without limiting it in any way.

EXAMPLES

1. General 1.1. Preparation of a mixture of compounds I to III 100 g of 8α,12-dihydroxy-13,14,15,16-tetranorlabdane were introduced with stirring into 500 ml of acetanhydride. After the addition of 30 drops of concentrated sulfuric acid, the acetylation reaction began, as reflected in discoloration and an increase in the temperature of the reaction mixture to around 50° C. After 7 hours, 300 ml of water were added and the reaction mixture was extracted three times with 100 ml of methyl-t-butyl ether. The combined ether extracts were washed with sodium hydrogen carbonate solution, dried over sodium sulfate and distilled at 150° C./0.04 mbar. 25 g of potassium hydroxide dissolved in 200 ml of methanol were then added with stirring to the main fraction obtained (75 g). After stirring for 24 hours, 300 ml of water were added and the whole was extracted three times with 200 ml of dichloromethane. The organic phase was then concentrated in vacuo. The yield (sum total of compounds I to III) amounted to 64 g. According to $^{13}$C-NMR, the isomers I, II and III were present in a ratio of 2:3.5:3.

1.2. Analysis

The products were quantified by gas chromatographic analysis (50 m WG11 quartz capillary; injector temperature 220° C., detector temperature 250° C., oven temperature 80→220° C. for a heating rate of 8° C./minute; carrier gas nitrogen; pressure 20 psi). 2. Test descriptions Example 1

2.5 g of the mixture of compounds I to III (cf. No. 1.1) were dissolved in 25 ml of dichloromethane and 1.6 g of p-toluene sulfonic acid were added to the resulting solution. After stirring for 7 hours at room temperature, a gas chromatogram of the reaction mixture showed 63% of Ambroxan and 20% of 8-epi-Ambroxan.

Example 2

The procedure was as in Example 1, except that 0.8 g of methane sulfonic acid was used as the catalyst. After stirring for 2 hours at room temperature, the reaction mixture contained 83% of Ambroxan and 6% of 8-epi-Ambroxan.

We claim:

1. A process for the production of 8α,12-oxido-13,14,15,16-tetranorlabdane comprising the step of cyclizing a mixture comprising at least 10% by weight of each of the compounds (I), (II) and (III):

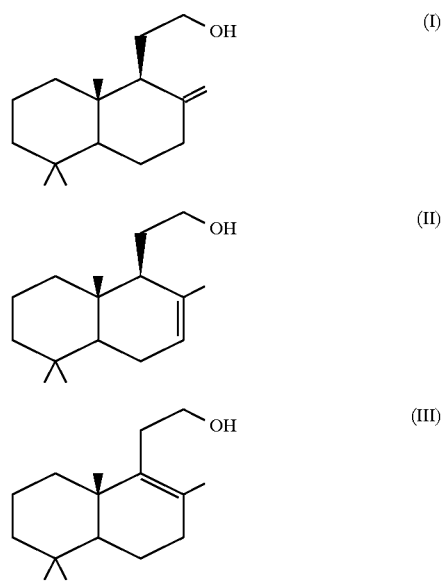

in the presence of 10% to 100% by weight of methane sulfonic acid, said amount of acid being based on the weight of said mixture of compounds (I), (II) and (III).

2. A process as claimed in claim 1, wherein said acid is present in an amount of 30% to 60% by weight based on the weight of said mixture of compounds (I), (II) and (III).

3. A process as claimed in claim 1, wherein said cyclizing is carried out at a temperature of −10° to 30° C.

4. A process as claimed in claim 2, wherein said cyclizing is carried out at a temperature of −10° to 30° C.

5. A process as claimed in claim 1, wherein said cyclizing step is carried out in the presence of a solvent selected from the group consisting of toluene, xylene, and halogenated hydrocarbons.

6. A process as claimed in claim 5, wherein said solvent is dichloromethane.

7. A process according to claim 1, wherein the mixture is cyclized in the presence of 30% to 40% by weight of methane sulfonic acid.

* * * * *